United States Patent [19]

Dolling et al.

[11] Patent Number: 5,786,515
[45] Date of Patent: Jul. 28, 1998

[54] SYNTHESIS OF α-CHLORO OR FLUORO KETONES

[75] Inventors: Ulf H. Dolling, Westfield; Lisa F. Frey, Piscataway; Richard D. Tillyer, Westfield; David M. Tschaen, Holmdel, all of N.J.

[73] Assignee: Merck & Co., Inc., Rahway, N.J.

[21] Appl. No.: 706,041

[22] Filed: Aug. 30, 1996

Related U.S. Application Data

[60] Provisional application No. 60/003,823, Sep. 15, 1995.
[51] Int. Cl.[6] .................................................... C07C 45/62
[52] U.S. Cl. ........................ 568/316; 544/242; 544/406; 546/298; 548/200; 548/255; 548/266.8; 548/335.1; 548/374.1; 548/469; 548/530; 549/70; 549/462; 549/473; 568/335; 568/382; 568/383; 568/393; 564/209
[58] Field of Search ........................... 570/185, 182, 570/187; 568/316, 335, 382, 383, 393; 564/209; 544/406, 242; 546/298; 548/335.1, 469, 200, 374.1, 530, 266.8, 255; 549/462, 483, 70

[56] References Cited

U.S. PATENT DOCUMENTS 4,385,177  5/1983  Foxton et al. ............................. 544/22

FOREIGN PATENT DOCUMENTS

WO 95/00501  1/1995  WIPO.

OTHER PUBLICATIONS

Comprehensive Organic Synthesis, Pergamon 1991, vol. 1, 397.
Friour, et al, Synthesis, 37, 1984.
Hirao, et al, Tetrahedron Lett., 929, 1986.
Nuzillard, et al, Tetrahedron Lett., 30(29) 3779, (1989).
Tillyer, et al, Synlett, vol. 96 (3), pp. 225–226 (Mar., 1996).
Nahm, et al, Tetrahedron Lett., vol. 22 (39), pp. 3815–3818, (1981).

*Primary Examiner*—Shailendra Kumar
*Attorney, Agent, or Firm*—Richard C. Billups; David L. Rose

[57] ABSTRACT

A simple, high yielding synthesis of a-chloro ketones is described, involving acylation of Grignard and organolithium reagents with N-methoxy-N-methylchloroacetamide. The efficiency of the process is further enhanced by recycling N,O-dimethylhydroxylamine.

8 Claims, No Drawings ents.

SYNTHESIS OF α-CHLORO OR FLUORO KETONES

This application is a continuation of Provisional Application No. 60/003,823, filed Sep. 15, 1995.

BACKGROUND OF THE INVENTION

This application is directed to an improved process for making α-chloro ketones such as 4-(methylthio)-2-chloroacetophenone, which compounds are intermediates useful in the preparation of certain non-steroidal anti-inflammatory agents. See, for example, WO 95/00501, published Jan. 5, 1995, which is hereby encorporated by reference.

The synthesis of α-chloro ketones such as 4-(methylthio)-2-chloroacetophenone 1

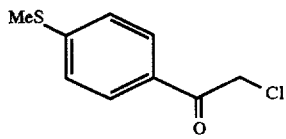

via Friedel-Crafts acylation of thioanisole with chloroacetic acid derivatives, and via direct halogenation of 4-(methylthio)acetophenone is possible, but both of these approaches are problematic. For example, while the Friedel-Crafts acylation of thioanisole using acetyl chloride-AlCl$_3$ is an efficient process (>90% yield, 100:1 para:ortho), the use of AlCl$_3$-chloroacetyl chloride is not (<40% yield, 3:1 para:ortho). The situation is not improved by variation of Lewis acid, solvent, or by the use of other chloroacetic acid derivatives. Similarly, the direct halogenation of 4-(methylthio)acetophenone is accompanied by the formation of (usually >10%) di-halogenated ketone, which was difficult to remove by crystallisation.

Moreover, of the many literature protocols for ketone synthesis based on acylation of organometallic reagents, they are generally inapplicable to the synthesis of a-halogenated ketones. See Comprehensive Organic Synthesis, Pergamon 1991, Volume 1, 397 and Friour G., Cahiez G., Normant J. F. Synthesis 37 1984, or organovanadium reagents—Hirao T., Misu D., Yao K., Agawa T., Tetrahedron Lett. 929, 1986. Not surprisingly, the reactions of organometallic reagents 2 (M=Li, MgBr, ZnBr/Cl, MnCl, etc.) with a variety of chloroacetic acid derivatives 3 (e.g. acid chloride, anhydride, imidazolide and nitrile) provided 1 in low yield, due primarily to over-addition and/or enolisation of product by the reagent.

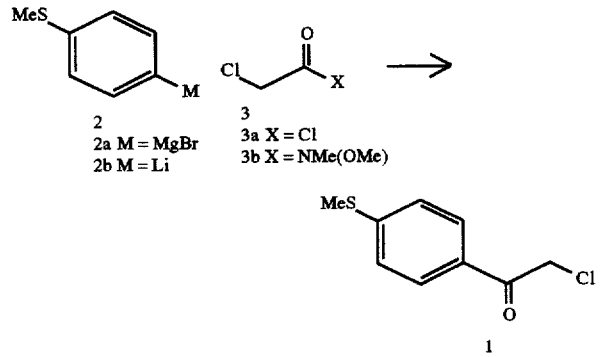

Surprisingly, we have found a novel and efficient synthesis of 1, and other α-chloro ketones via reaction of N-methoxy-N-methylchloroacetamide 3b with organometallic reagents.

SUMMARY OF THE INVENTION

The invention is directed to a process for making α-chloro or α-fluoro ketones, such as 4-(methylthio)-2-chloroacetophenone, which compounds are intermediates useful in the preparation of non-steroidal anti-inflammatory agents.

DETAILED DESCRIPTION OF THE INVENTION

The invention encompasses an improved process for making α-chloro ketones, or α-fluoro ketones, including 4-(methylthio)-2-chloroacetophenone, which compounds are intermediates useful in the preparation of non-steroidal anti-inflammatory agents.

In one embodiment, the invention is directed to a process of making an α-chloro or fluoro ketone of the formula I

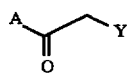

wherein Y is chloro or fluoro and A is a carbon nucleophile, comprising:

(a) reacting an organometallic reagent of formula II

wherein M is Li or Mg, with a compound of formula III

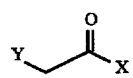

wherein X is —NR(OR$^1$) R and R$^1$ are each independently linear or branched C$_{1-3}$ alkyl, C$_{3-6}$cycloalkyl, form a ring, or optionally substituted with C$_{1-3}$alkoxy, phenyl, subtstituted phenyl, wherein the substituent on the phenyl is selected from F, Cl, Br, methylthio, —OH, methoxy, aminothio, and C$_{1-3}$ alkyl.

in an organic aprotic solvent, and (b) reacting, without further purification, the product of step (a) with an aqueous solution of acid G, to yield an organic aprotic solvent phase comprising compound of formula I and an aqueous solvent phase comprising compound of formula III'

In a preferred aspect of this invention Y is chloro.

The aqueous and organic phases may be separated by standard liquid-liquid separation means, such as by decantation or centrifugation.

For purposes of this specification, the acid G includes, but is not limited to hydrochloric, hydrobromic, sulfuric, methanesulfonic, toluenesulfonic, phosphoric acid, and the like.

For purposes of this specification the organic aprotic solvent includes, but is not limited to ethereal solvents including diethyl ether, di-n-butyl and di-isopentyl ethers, anisole, cyclic ethers such as tetrahydropyran, 4-methyl-1,3-dioxane, tetrahydrofurfuryl methyl ether, ethyl ether, furan, and tetrahydrofuran.

For purposes of this specification the carbon nucleophile A is defined to include optionally substituted:

(1) phenyl,
(2) 3,4-dimethoxyphenyl,
(3) benzofuranyl,
(4) furanyl,
(5) imidazolyl,
(6) indolyl,
(7) isothiazolyl,
(8) pyrazinyl,
(9) pyrazolyl,
(10) pyridyl,
(11) pyrimidyl,
(12) pyrrolyl,
(13) thiazolyl,
(14) thienyl,
(15) triazolyl,
(16) $C_{1-10}$ alkyl,
(17) $C_{2-3}$alkenyl
(18) $C_{2-3}$alkynyl, wherein the substitutent is selected from F, Cl, Br, methylthio, —OH, methoxy, aminothio, $C_{1-3}$ alkyl, $C_{2-3}$alkenyl, $C_{2-3}$alkynyl.

The reaction step (a) is allowed to proceed until substantially complete in 10 min to 3 hr. The molar ratio of formula II to compound of formula III is typically 1:1 or greater (i.e. excess amount of formula II); preferably 1:1 to 1.2:1. The reaction may be conducted to –30° to 20° C.; preferably 0° to 10° C.

The reaction step (b) is allowed to proceed until substantially complete in 5 min. to 3 hr; typically on the order of 15 minutes. The molar ratio of acid to compound of formula III is typically 1:1 or greater (excess acid); preferably 1:1 to 1.2:1. The reaction may be conducted at –10° to 20° C.; preferably 0° to 5° C.

Within this aspect, there is a class of process wherein the compound of formula I is

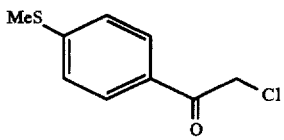

the compound of formula II is

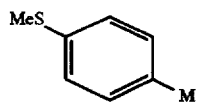

and X is —NCH$_3$(OCH$_3$).

In a second aspect, the invention is directed to a process of making a compound of formula III

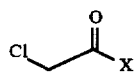

wherein X is —NR(OR$^1$) wherein R and R$^1$ are described as above, comprising acylating HNR(OR$^1$) hydrochloride with chloroacetyl chloride in a two phase mixture of aqueous base and a non-reactive water insoluble organic solvent to yield a compound of formula III.

For purposes of this specification, the base includes both organic bases including pyridine, tri-$C_{1-3}$ alkylamine, and inorganic bases include sodium hydroxide, potassium hydroxide, sodium carbonate or bicarbonate or potassium carbonate or bicarbonate.

For purposes of this specification the non-reactive water insoluble organic solvent includes, but is not limited to toluene, methyl t-butyl ether (MTBE), hexane, heptane, methylene chloride, dichloroethane, dichlorobenzene, monochlorobenzene.

The reaction is allowed to proceed until substantially complete in 5 min. to 1 hr. The molar ratio of HNR(OR$^1$) to chloroacetyl chloride is typically 1:1 or greater (i.e. excess chloroacetyl chloride); preferably 1.1:1 to 1.2:1. The reaction is conducted at –10° to 20° C.; preferably 0° to 5° C.

A preferred procedure for making a compound of formula III comprising: separating from the product of reaction step (b) the aqueous solvent phase, said aqueous solvent phase comprising compound of formula III', and reacting, without further purification, the aqueous solvent phase with chloroacetyl chloride in a bi-phasic mixture of aqueous K$_2$CO$_3$ and MTBE or toluene, to yield a compound of formula III.

The reaction is allowed to proceed until substantially complete in 5 to 50 minutes. The molar ratio of I' to K$_2$CO$_3$ is typically 1:2 to 1:3 (i.e. excess base); preferably 1:2.5. The concentration of chloroacetyl chloride in the organic solvent (MTBE or toluene) is 0.2–0.5 M, preferably 0.5 M. The ratio of organic solvent to aqueous solution is 1:1 to 2:1 (excess organic solvent), preferably 1:1. The reaction is conducted to –10° to 5° C.; preferably 0° to 5° C.

One objective of the invention was to develop a practical synthesis of the amide 3b. A non-aqueous acylation (Et$_3$N, CH$_2$Cl$_2$) of N,O-dimethylhydroxylamine hydrochloride with chloroacetyl chloride has been reported. See Nuzillard J.-M., Boumendjel G., Massiot G. Tetrahedron Lett., 30 (29) 3779, 1989. This was accomplished via acylation of N,O-dimethylhydroxylamine hydrochloride with chloroacetyl chloride, using a two phase mixture of aq K$_2$CO$_3$ and toluene/MTBE. The highly pure amide 3b was isolated in excellent yield (95%) after solvent removal (when MTBE used as solvent). For large scale runs the amide 3b (prepared using toluene as solvent) was used directly as a solution in toluene (after azeotropic drying) for reactions with organometallic reagents.

Reaction of the amide 3b with the Grignard reagent 2a (1M solution in THF, 1.2 equiv., prepared from 4-bromothioanisole) proceeded cleanly and rapidly in THF (reaction complete within 1.5 h at 25° C.) to give, after aqueous workup (2N HCl), 4-(methylthio)-2-chloroacetophenone 1 in 90% yield. [Yield determined by quantitative HPLC analysis of the organic layer after workup, compared to a standard solution of chromatographed ketone 1.] No over addition was observed, and the only significant (>0.5%) by-products were derived from preparation of the Grignard reagent. [By-products from the Grignard formation included the corresponding phenol (oxidation) and biaryl (homocoupling). The former was significantly reduced by de-gassing the reaction solvent and the HCl used for quench.] The crude product was crystallised from toluene-hexane (1:2) to give 1 in 80% yield (>98% purity by HPLC analysis).

A drawback commonly associated with the use of N-methoxy-N-methyl amides for ketone synthesis is the high cost of N,O-dimethylhydroxylamine hydrochloride. Although aqueous workup regenerates N,O-dimethylhydroxylamine (or its hydrochloride salt), there are few, if any, reports concerning its recovery from the aqueous extract. Recycling of this material is now possible via direct acylation of N,O-dimethylhydroxylamine in the aqueous extract with chloroacetyl chloride. Thus, after workup (aq HCl) the aqueous extract was reacted with chloroacetyl chloride-K$_2$CO$_3$ to give the amide 3 cleanly (80% yield based on N,O-dimethylhydroxylamine hydrochloride used initially). This material was re-used in reactions with Grignard reagent 2a to give 1 without loss in yield or product purity.

The Following examples are intended to illustrate, but not limit the invention as disclosed herein:

EXAMPLE 1

Procedure for the preparation of the 4-(methylthio-2-chloroacetophenone (1)

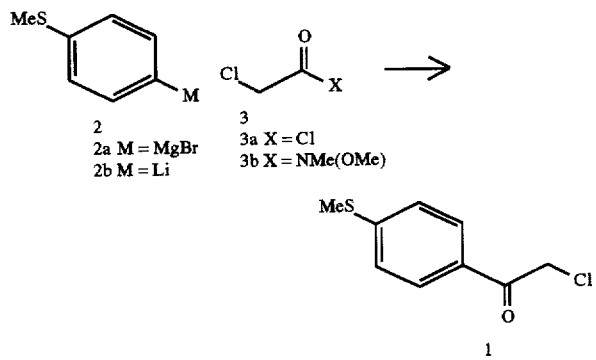

A solution of N-methoxy-N-methylchloroacetamide 3b (26.8 g, 195 mmol) in toluene (250 mL, see ref 9) was diluted with de-gassed THF (530 mL) and the mixture was cooled to 0° C. A solution of the Grignard reagent 2a (240 mL of a 1M soln in THF, 1.2 equiv.) was added, via cannula, over 30 min (solution temperature <5° C.) and the mixture was stirred at 25° C. for 1.5 h. The thick slurry was transferred, via cannula, into cold (0° C.), de-gassed aq. 2N HCl (250 mL, 2.5 equiv.) and the layers were separated. The organic layer was washed with brine (100 mL), dried (MgSO$_4$), filtered and concentrated (to approx. 75 mL). Hexanes (150 mL) was added and the mixture was stirred for 2 h. The slurry was filtered, the solid was washed with hexanes and dried to give 32.9 g (80% from N,O-dimethylhydroxylamine hydrochloride) of 1, a yellow solid.

$^1$NMR (CDCl$_3$, 300 MHz) $\partial$2.53 (s, 3H), 4.67 (s, 2H), 7.28 (d, 2 H, J=8.5 Hz), 7.87 (d, 2H, J=8.6 Hz); $^{13}$C NMR (CDCl$_3$, 75 MHz) $\partial$ 14.69, 45.77, 125.07, 128.95, 130.35, 147.48, 190.16.

The aqueous layer was added to a biphasic mixture of K$_2$CO$_3$ (79 g, 570 mmol) in H$_2$O (200 mL) and MTBE (500 mL) to give a heavy slurry. The vigorously stirred mixture was cooled to −5° C. and chloroacetyl chloride (19.6 mL, 246 mmol) was added, over 5 min (solution temperature <1° C.). The mixture was warmed to 5° C. over 30 min, the layers were separated and the aqueous layer was extracted with MTBE (5×100 mL). The combined organic extracts were concentrated to give 22.7 g (80% based on 20 g of N,O-dimethylhydroxylamine hydrochloride used initially) of amide 3b. This material was identical spectroscopically and by HPLC analysis to 3b prepared from fresh N,O-dimethylhydroxylamine hydrochloride.

The reactions listed as Examples 2 through 6 (Table I) were conducted using the procedure of Example 1 with appropriate substitution of reagent 2.

TABLE 1

| Example | Reagent | product | yield[1] |
|---|---|---|---|
| 1 | 2a(2b) | MeS-C$_6$H$_4$-C(O)-CH$_2$-Cl | 90 (92%)[2] |
| 2 | methylenedioxyphenyl-MgBr | methylenedioxyphenyl-C(O)-CH$_2$-Cl | 83 (76)[2] |
| 3 | Ph-MgBr | Ph-C(O)-CH$_2$-Cl | 92 |
| 4 | 2-thienyl-Li | 2-thienyl-C(O)-CH$_2$-Cl | 87 |
| 5 | C$_8$H$_{18}$MgBr | C$_8$H$_{18}$-C(O)-CH$_2$-Cl | 95 |
| 6 | Ph—≡—Li | Ph—≡—C(O)-CH$_2$-Cl | 86[3] |

[1]Isolated yield after chromatography;
[2]Yields in brackets correspond to reactions involving organolithium reagents;
[3]Reaction carried out at −10° C. for 45 min.

EXAMPLE 2

A solution of N-methoxy-N-methylchloroacetamide 3b (1.65 g, 12 mmol) in toluene (15 mL) was diluted with de-gassed THF (27 mL) and the mixture was cooled to 0° C. A solution of the Grignard reagent (14.4 mL of a 1M soln in THF, 1.2 equ, prepared from the reaction of 4-bromo-1,2-(methylenedioxy) benzene with Mg in THF) was added, via cannula, over 30 min (solution temperature <5° C.) and the mixture was stirred at 25° C. for 2.5 h. The mixture was transferred, via cannula, into cold (0° C.), de-gassed aq. 2N HCl (35 mL, 5.8 equ), diluted with tolune (10 mL), and the layers were separated. The organic layer was washed with brine (20 mL), dried (MgSO$_4$), filtered and concentrated to give the product in 83% yield.

A solution of 4-bromo-1,2-(methylenedioxy) benzene (2.2 mL, 18 mmol) in de-gassed THF (50 mL) was cooled to −78° C. and n-BuLi (11.3 mL of 1.6M soln, 1.2 equ) was added. After stirring for 50 min at −50° C., a solution of N-methoxy-N-methylchloroacetamide 3b (2.06 g, 15 mmol) in de-gassed THF (14 mL) was slowly added, and the mixture was aged 1 h at −20° C. The mixture was transferred, via cannula, into cold (0° C.), de-gassed aq. 2N HCl (37.5 mL, 5.0 equ), diluted with ethyl acetate (20 mL), and the layers were separated. The organic layer was washed with brine (20 mL), dried (MgSO4), filtered and concentrated to give the product in 76% yield. 1H NMR (CDCl3, 300 MHz) ∂4.62 (s, 2H), 6.06 (s, 2H), 6.86 (d, 1H, J=8.1 Hz), 7.41 (d, 1H, J=1.8Hz), 7.54 (m, 1H; 13 C NMR (CDCl3) a 45.76, 102.16, 108.17, 108.26, 125.08, 128.91, 148.49, 152.59, 189.28.

EXAMPLES 3 TO 5

Following the procedures of Examples 1 and 2 using the reagents listed in Table 1, the corresponding product was produced.

EXAMPLE 6

A solution of phenyl acetylene (2.0 mL, 18 mmol) in de-gassed THF (30 mL) was cooled to −78° C. and n-BuLi (11.3 mL of 1.6M soln, 1.5 equ) was added. After stirring for 20 min, the solution was allowed to warm to −20° C. A solution of N-methoxy-N-methylchloroacetamide 3b (1.65 g, 12 mmol) in de-gassed THF (13 mL) was slowly added, and the mixture was aged 15 min at −20° C. followed by 45 min at −10° C. The mixture was transferred, via cannula, into cold (0° C.), de-gassed aq. 2N HCl (35 mL, 5.8 equ), diluted with ethyl acetate (10 mL), and the layers were separated. The organic layer was washed with brine (20 mL), dried (MgSO4), filtered and concentrated. After silica gel chromatography (97:3 hexanes:ethyl acetate), the compound was isolated in 86% yield. $^1$H NMR (CVDc13, 300 MHz) ∂4.33 (s, 2H), 7.41 (m, 2H), 7.51 (m, 1H), 7.62 (m, 2H); $^{13}$C NMR (CDCl 3) 49.53, 85.55, 95.40, 119.22, 128.79 (2C), 131.46, 133.40 (2C), 178.89.

We have extended this chemistry to the preparation of α-monofluoro ketones via reaction of organometallic reagents with N-methoxy-N-methylfluoroacetamide (5). For example, phenacyl fluoride (6) was prepared in 88% yield via reaction of 5 with phenylmagnesium bromide. Many other extensions of this chemistry should be possible.

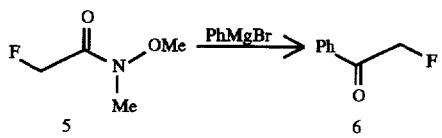

In summary, we have described a practical synthesis of N-methoxy-N-methylchloroacetamide 3b and have shown that this compound reacts cleanly with Grignard and organolithium reagents to produce α-monochloro ketones in high yield. The ability to recycle the N,O-dimethylhydroxylamine in a highly efficient manner increases cost effectiveness and makes this procedure particularly attractive for large scale synthesis.

EXAMPLE 7

Preparation of N-methoxy-N-methylchloroacetamide (3b).

To a cold (0° C.), stirred solution of K$_2$CO$_3$ (62.4 g, 450 mmol) in H$_2$O (250 mL) was added, successively, N,O-dimethylhydroxylamine hydrochloride (20 g, 205 mmol) and organic solvent (250 mL, toluene or MTBE). The resulting two phase mixture was cooled to −5° C. and chloroacetyl chloride (19.6 ml, 246 mmol) was added over 5 min (solution temperature maintained below 0° C.). The vigorously stirred mixture was allowed to warm to 15° C. over 30 min, the layers were separated, and the aqueous layer was extracted with organic solvent (3×100 mL, toluene or MTBE). The combined organic extracts were concentrated (MTBE used as solvent) to give the amide 3b (26.8 g, 95%) as a white solid. Alternatively, the combined organic extracts (toluene used as solvent) were concentrated to 250 mL to effect azeotropic drying (water content 100 μg/mL) and the solution of 3b was used directly in reactions with organometallic reagents.

What is claimed is:

1. A process of making an a-chloro or fluoro ketone of the formula I

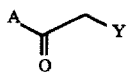

wherein Y is chloro or fluoro and A is a carbon nucleophile, comprising:

(a) reacting an organometallic reagent of formula II

wherein M is Li or Mg, with a compound of formula III

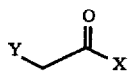

wherein X is —NR(OR$^1$) R and R$^1$ are each independently linear or branched C$_{1-3}$ alkyl, C$_{3-6}$cycloalkyl, or optionally substituted with C$_{1-3}$alkoxy, phenyl, subtstituted phenyl, wherein the substituent on the phenyl is selected from F, Cl, Br, methylthio, —OH, methoxy, aminothio, and C$_{1-3}$ alkyl in an organic aprotic solvent, and (b) reacting, without further purification, the product of step (a) with an aqueous solution of acid G, to yield an organic aprotic solvent phase comprising compound of formula I and an aqueous solvent phase comprising compound of formula III'

2. A process according to claim 1 wherein Y is chloro and acid G is selected from the group consisting of hydrochloric, hydrobromic, sulfuric, methanesulfonic, toluensulfonic, phosphoric acid.

3. A process according to claim 1 wherein the organic aprotic solvent is selected from the group consisting of diethyl ether, di-n-butyl and di-isopentyl ethers, anisole, cyclic ethers such as tetrahydropyran, 4-methyl-1,3-dioxane, tetrahydrofurfuryl methyl ether, ethyl ether, furan, and tetrahydrofuran or a mixture thereof.

4. A process according to claim 1 wherein the carbon nucleophile A is an optionally substituted:

(1) phenyl,
(2) 3,4-dimethoxyphenyl,
(3) benzofuranyl,
(4) furanyl,
(5) imidazolyl,
(6) indolyl,
(7) isothiazolyl,
(8) pyrazinyl,
(9) pyrazolyl,
(10) pyridyl,
(11) pyrimidyl,
(12) pyrrolyl,
(13) thiazolyl,
(14) thienyl,
(15) triazolyl,
(16) $C_{1-10}$ alkyl,
(17) $C_{2-3}$ alkenyl
(18) $C_{2-3}$ alkynyl, wherein the substitutent is selected from F, Cl, Br, methylthio, —OH, methoxy, aminothio, $C_{1-3}$ alkyl, $C_{2-3}$ alkenyl or $C_{2-3}$ alkynyl.

5. A process according to claim 4 wherein the carbon nucleophile is an optionally substituted:

(1) phenyl,
(2) 3,4-dimethoxyphenyl,
(3) benzofuranyl,
(4) thienyl,
(5) $C_{1-10}$ alkyl,
(6) $C_{2-3}$ alkenyl
(7) $C_{2-3}$ alkynyl, wherein the substitutent is selected from F, Cl, Br, methylthio, —OH, methoxy, aminothio and $C_{1-3}$ alkyl.

6. A process according to claim 1 wherein R and $R^1$ are each selected from linear or branched $C_{1-3}$ alkyl, $C_{3-6}$ cycloalkyl, or optionally substituted with $C_{1-3}$ alkoxy, phenyl, substituted phenyl, wherein the substituent on the phenyl is selected from F, Cl, Br, methylthio, —OH, methoxy, aminothio, and $C_{1-3}$ alkyl.

7. A process according to claim 1 wherein the compound of formula I is

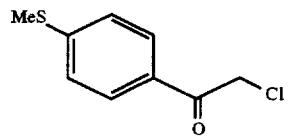

the compound of formula II is

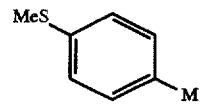

8. A process of making an α-chloro or fluoro ketone of the formula I

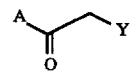

wherein Y is chloro or fluoro and A is a carbon nucleophile, comprising:

(a) reacting an organometallic reagent of formula II

A—M wherein M is Li or Mg, with a compound of formula III

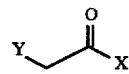

wherein X is —NR(OR$^1$) R and $R^1$ are each independently linear or branched $C_{1-3}$ alkyl, $C_{3-6}$ cycloalkyl, or optionally substituted with $C_{1-3}$ alkoxy, phenyl, subtstituted phenyl, wherein the substituent on the phenyl is selected from F, Cl, Br, methylthio, —OH, methoxy, aminothio, and $C_{1-3}$ alkyl in an organic aprotic solvent, and (b) reacting, without further purification, the product of step (a) with an aqueous solution of acid G, to yield an organic aprotic solvent phase comprising compound of formula I and an aqueous solvent phase comprising compound of formula III

HNR(OR$^1$)·G:    III separating the organic phase to obtain a Compound of formula I and acylating the aqueous phase containing HNR(OR$^1$) hydrochloride with chloroacetyl chloride in a two phase mixture of aqueous base and a non-reactive water insoluble organic solvent to yield a compound of formula II where the two phase mixture is recycled and reacted with a compound of formula II to continuously repeat the preparation of the compound of formula I.

* * * * *